United States Patent [19]

Stone et al.

[11] Patent Number: 5,394,888
[45] Date of Patent: Mar. 7, 1995

[54] ARTHROMETER WITH GRAVITY SWITCHES AND ADJUSTABLE LIMIT SIGNALING

[76] Inventors: Kevin R. Stone, 1 Throckmorton La., Mill Valley, Calif. 94941; Perry A. Klebahn, 2633 Steiner St., San Francisco, Calif. 94115; William R. Knapp, 116 Gilbert St., Menlo Park, Calif. 94025

[21] Appl. No.: 992,059

[22] Filed: Dec. 17, 1992

[51] Int. Cl.$^6$ ............................................. A61B 5/103
[52] U.S. Cl. .................................. 128/782; 482/909; 340/573
[58] Field of Search .................. 482/909; 128/782; 340/573, 689; 73/379.01, 865.4; 33/373, 384; 200/220, 230

[56] References Cited

U.S. PATENT DOCUMENTS

| | | |
|---|---|---|
| 1,590,499 | 6/1926 | Cozad . |
| 2,565,381 | 8/1951 | Leighton ............................ 33/221 |
| 3,020,639 | 2/1962 | Karpovich et al. ................... 33/1 |
| 3,229,372 | 1/1966 | Quashnock et al. ................. 33/75 |
| 3,362,023 | 1/1968 | McMahon ........................ 340/573 |
| 3,482,186 | 12/1969 | Del Vecchio, Jr. et al. ...... 200/220 |
| 4,201,226 | 5/1980 | Phillips ............................. 128/774 |
| 4,306,571 | 12/1981 | McLeod, Jr. ..................... 128/782 |
| 4,461,085 | 7/1984 | Dewar et al. ...................... 33/174 |
| 4,485,825 | 12/1984 | Domjan et al. ................... 128/774 |
| 4,557,275 | 12/1985 | Dempsey, Jr. ..................... 128/782 |
| 4,583,555 | 4/1986 | Malcom et al. ................... 128/774 |
| 4,663,856 | 5/1987 | Hall et al. .......................... 33/373 |
| 4,665,388 | 5/1987 | Ivie et al. .......................... 428/909 |
| 4,712,542 | 12/1987 | Daniel et al. ...................... 128/92 |
| 4,743,028 | 5/1988 | Harrison .......................... 340/573 |
| 4,804,001 | 2/1989 | McLeod, Jr. ..................... 128/782 |
| 4,834,057 | 5/1989 | McLeod, Jr. ..................... 128/782 |
| 4,899,133 | 2/1990 | Barlett ............................. 340/573 |
| 4,911,177 | 3/1990 | Lamb et al. ...................... 128/782 |
| 4,958,145 | 9/1990 | Morris ............................. 340/689 |
| 4,969,471 | 11/1990 | Daniel et al. ..................... 128/774 |
| 5,128,655 | 7/1992 | Shore ............................... 128/782 |
| 5,146,206 | 9/1992 | Callaway ......................... 128/782 |

FOREIGN PATENT DOCUMENTS 55-95804 of 0000 Japan .
0023027 2/1913 Norway ............................. 33/384

OTHER PUBLICATIONS

Townsend et al., "Total Motion knee Goniometry," J. Biomechanics, vol. 10, No. 3, pp. 183–193.
Chao et al., "Instrumented Measurement of Human Joint Motion," ISA Transactions, vol. 17, No. 1, pp. 13–19.
Kettelkamp et al., "An Electrogoniometric Study of Knee Motion in Normal Gait," The Journal of Bone and Joint Surgery, vol. 52-A, No. 4, pp. 775–790.

*Primary Examiner*—Richard J. Apley
*Assistant Examiner*—Jeanne M. Mollo
*Attorney, Agent, or Firm*—Lappin & Kusmer

[57] ABSTRACT

An apparatus for measuring the angle of flexure between an elongated body limb and the portion of the body to which the limb is affected. The apparatus can be used to monitor flexure between a thigh and lower portion of a human leg. The apparatus is useful during the performance of rehabilitative knee-bends includes means for coupling the apparatus to the thigh, and two gravity actuated switches for monitoring the angle between a long axis of the thigh and a vertical axis. The apparatus indicates when the extreme points of the knee-bend have been crossed.

1 Claim, 5 Drawing Sheets

ARTHROMETER WITH GRAVITY SWITCHES AND ADJUSTABLE LIMIT SIGNALING

BACKGROUND OF THE INVENTION

The invention relates generally to an apparatus for monitoring the flexure angle between two jointed body limbs, for example, the knee flexure angle between a jointed thigh and lower portion of a human leg, as those limbs move in a vertical plane. In particular, the invention concerns a device useful for facilitating the monitoring of rehabilitative motions, such as knee bends.

Arthrometers measure joint motion. Generally, two types of arthrometers are currently available: passive arthrometers for measuring joint motion of another person, and automatic arthrometers for measuring one's own joint motion. Typically, passive arthrometers are referred to as goniometers.

The need to measure joint motion frequently occurs during rehabilitation therapy. For example, patients participating in post-operative therapy following knee surgery are often instructed to perform standing knee-bends from between, for example, 170 to 90 degrees. Similarly, after shoulder surgery, patients are often instructed to perform arm lifts over a predetermined range of motion in a vertical plane.

Prior art arthrometers are large, complex, and expensive. Large institutions can maintain such arthrometers, but once a patient is discharged from a health care facility, and such arthrometers are no longer available, the actual flexure angle of the patient's limbs are typically determined by mere guesswork.

Simple, automatic measurement of joint motion during exercise has not been heretofore available. Neither has there been available mechanisms for indicating actual range of motion and counting repetitions in an exercising cycle. Accordingly, individuals who have been discharged from a health care facility and instructed to maintain a therapeutic exercise regimen, have been faced with great difficulty in implementing that regimen.

It is therefore an object of the invention to provide a simple device for measuring joint motion which can be easily used by an unskilled operator. Another object of the invention is to provide such a device that is inexpensive, and does not interfere with the user's range of motion.

SUMMARY OF THE INVENTION

These and other objects are achieved by the present invention which in one aspect features an apparatus for monitoring the flexure angle between a limb and the body part (such as another limb) to which it is attached.

In the preferred embodiment, the apparatus includes a rigid housing and an associated device for coupling the housing to a portion of a user's leg and preferably to the thigh of a user so that the principal axis of the housing is substantially parallel to the long axis of the femur of the user's thigh. The apparatus also functions while being attached at other angles. Alternatively, the apparatus may be coupled to the lower leg of the user. The apparatus includes first and second gravity-actuated switches, each having at least two states. The switches are disposed in the housing for monitoring the angle between the principal axis and a vertical axis. Since in the preferred usage, the principal axis is substantially parallel to the long axis of the thigh, the switches effectively monitor the angle between the long axis of the thigh and the vertical axis which directly correlates to the angle of the knee joint (i.e., the angle between the long axis of the femur and the long axis of the tibia).

The first switch is arranged so that it is in its first state when its orientation is within a first range of orientations, and is in its second state when its orientation is within a second range of orientations. The second switch is arranged so that it is in its first state when its orientation is within a third range of orientations, and is in its second state when its orientation is within a fourth range of orientations. Each switch is disposed within a positioning assembly so that the orientation of the switches can be adjusted relative to the principal axis. The positioning assemblies allow two ranges of orientations to be preset such that the first switch will be in its first state when the orientation of the housing is within the first range of preset orientations, and will be in its second state otherwise, and the second switch will be in its first state when the orientation of the housing is within the second range of preset orientations, and will be in its second state otherwise. As a consequence, with the device attached to a limb, the switched change state an associated predetermined angles representative of limits of angular (with respect to a local vertical) motion of the limb.

In another form of the invention, the apparatus includes a mechanism for indicating or displaying the state of the switches, or changes in the states of the switches. The indication or display may be in the form of an audible tone, or as a visual optical signal.

A preferred use of the invention is to assist a user in performing a series of repetitive knee-bends. To perform the knee-bends the user squats down until the user's knee flexure angle reaches a specified lower extreme angle (e.g., 90 degrees) and then stands up until the user's knee flexure angle reaches a specified upper extreme angle (e.g., 170 degrees).

In one preferred embodiment the apparatus emits audible tones that inform the user when the upper and lower extreme points have been reached and indicates when the user should change direction. The audible tones may be different frequencies for high and low limits.

In another preferred embodiment the apparatus has a mechanism for counting the number of repetitions of knee-bends that have been performed.

The apparatus may also be attached to a user's upper arm, so that motion (in a vertical plane) may be monitored as the user alternately raises and lowers his arm. In this case, angular motion of the upper arm is monitored with respect to the user's shoulder. The apparatus may also be attached to a user's forearm, so that motion (in a vertical plane) may be monitored, for example, as the user performs curls. In this case, angular motion of the user's forearm is monitored with respect to his upper arm.

BRIEF DESCRIPTION OF THE DRAWINGS

The foregoing and other objects of this invention, the various features thereof, as well as the invention itself, may be more fully understood from the following description, when read together with the accompanying drawings in which.

DESCRIPTION OF THE ILLUSTRATED EMBODIMENT

Figure 1:
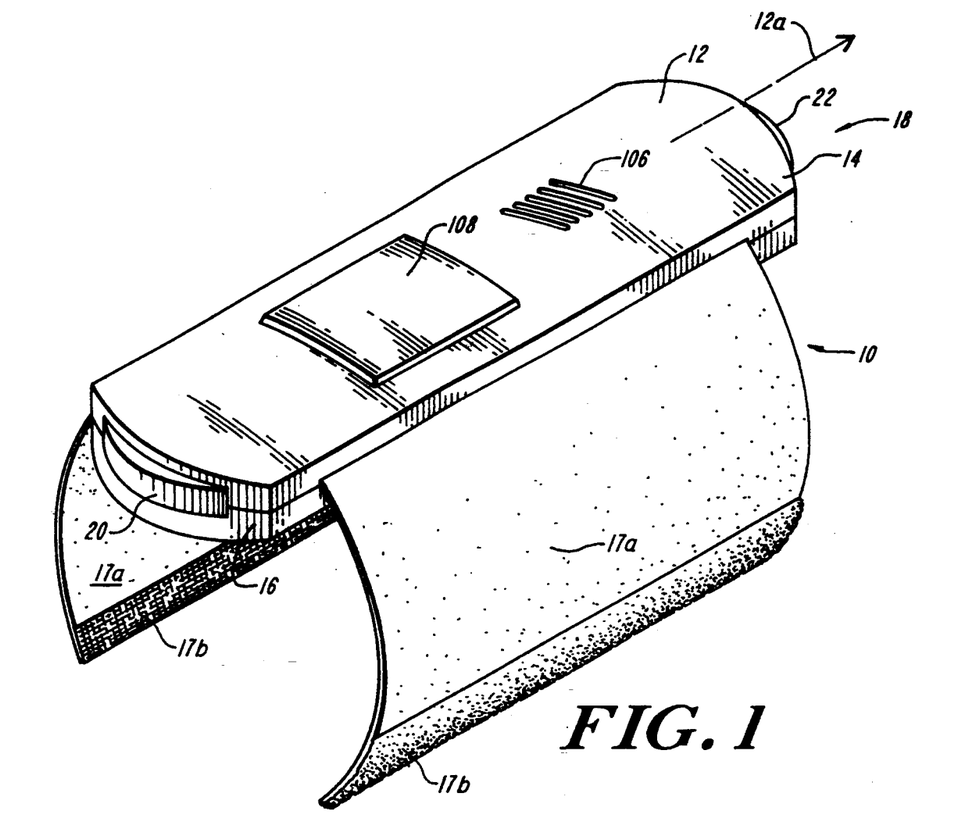
FIG. 1 is a perspective view of an arthrometer according to the invention.
Figure 2:
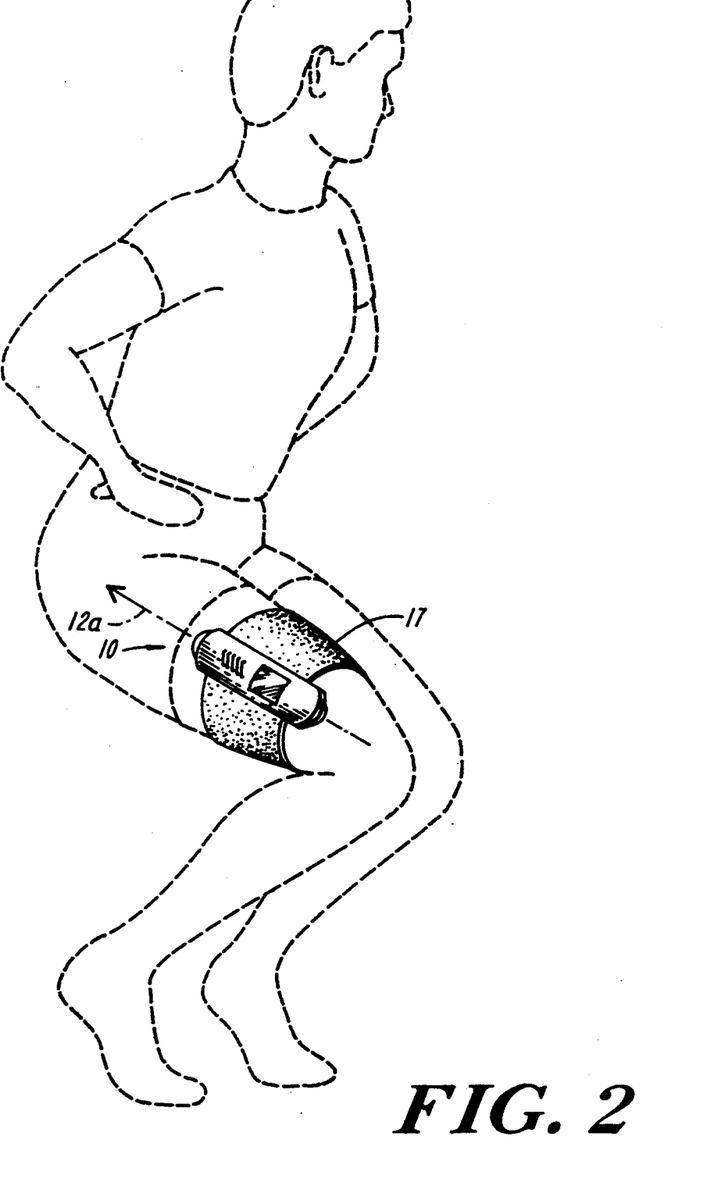
FIG. 2 illustrates the arthrometer of FIG. 1 attached to a thigh of a user.

FIG. 1 shows an arthrometer 10 according to the invention. The arthrometer 10 has a rigid housing 12 which has a generally elongated rectangular shape extending along a principal axis 12a with rounded top and bottom ends 14, 16, respectively. Switch positioning assemblies 18, 20 are disposed at each end. In operation, as shown in FIG. 2, a coupling mechanism 17 is used to attach the housing 12 to an elongated limb of a human body so that the principal axis 12a is at a fixed presentation (preferably parallel) to the long axis of the limb. The housing 12 may be affixed to a person's upper leg, lower leg, upper arm or lower arm, for example.

The coupling mechanism 17 includes flexible belts or straps 17a extending from the housing 12 with complimentary fasteners 17b at the distal tips. The fasteners may be of the "belt buckle", or "snap" type, "hook and loop" type, or other fastening type mechanism as are known in the art. Preferably, the lower surface (not shown) of housing 12 is concave along an axis parallel to axis 12a to provide a preferred seating of the housing substantially parallel to axis 12a. The housing 12 includes an alarm sounding device 106 and optionally a visual display 108.

Figure 3:
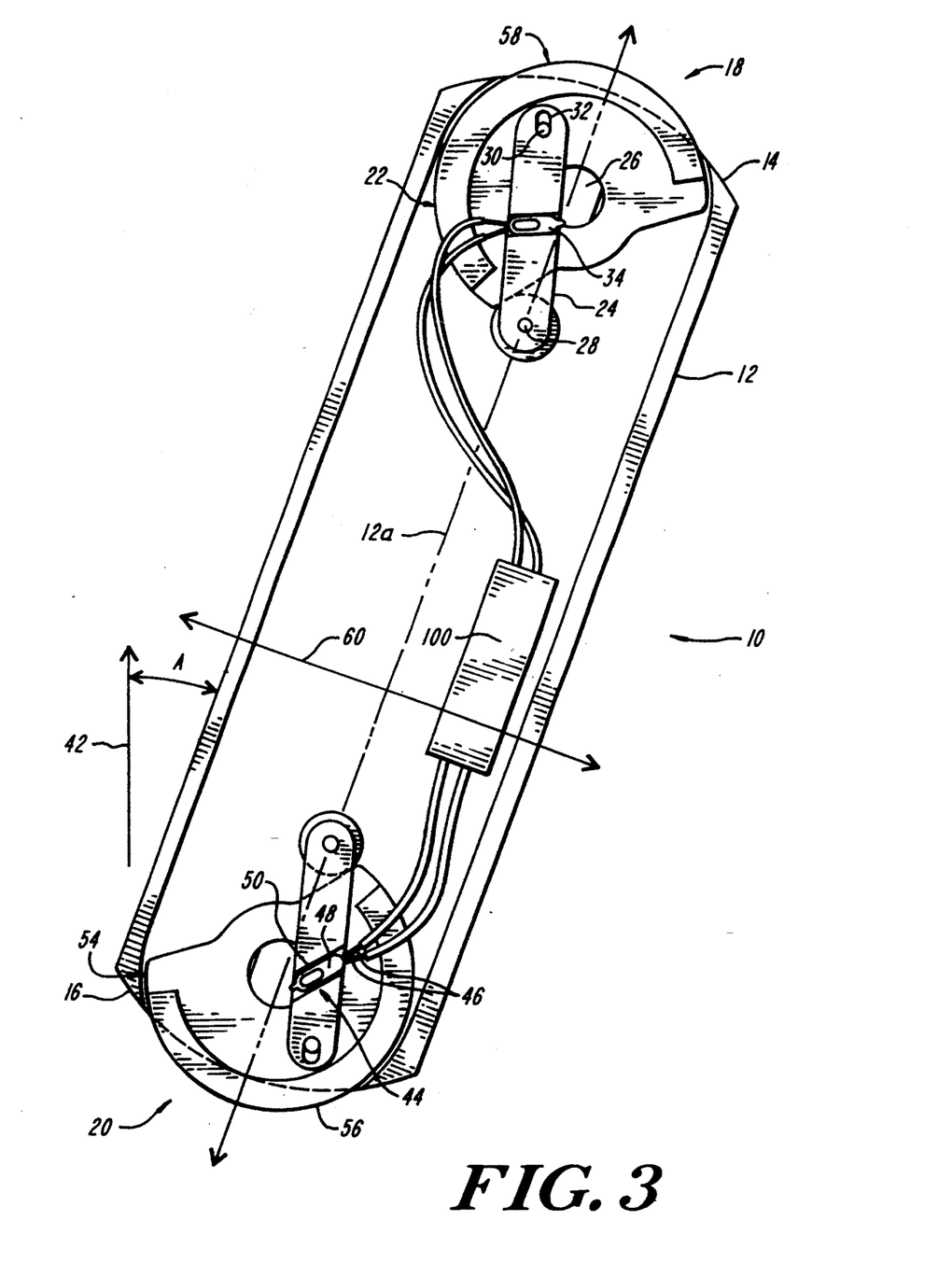
FIG. 3 is a cut-away side view of the arthrometer of FIG. 1.

As shown in the cut-away view of FIG. 3, the top switch positioning assembly 18 contains an adjustment dial 22 and an elongated arm 24 which together form an angle reduction assembly permitting a vernier-type adjustment. The dial 22 is rotatably mounted to the housing 12 at a shaft 26. One end of the arm 24 is rotatably mounted to the housing 12 at a shaft 28, and the other end of arm 24 is rotatably and slidably mounted to the dial 22 at a shaft 30 extending from the dial 22. The shaft 30 is rigidly affixed in the dial 22, and the shaft 30 is slidingly fitted within an elongated aperture 32 of the arm 24. A 2:1 angle reduction provides a suitable adjustment sensitivity, but other ratios, or no reduction can be used. Preferably, shafts 26, 28 and 30 extend along central axes that are perpendicular to the axis 12a. A gravity-actuated switch 34 is rigidly mounted to the arm 24 at a predetermined angle relative to the long axis of arm 24. In the preferred embodiment switch 34 is a mercury switch, although other types of gravity actuated switches can be used.

Figure 4:
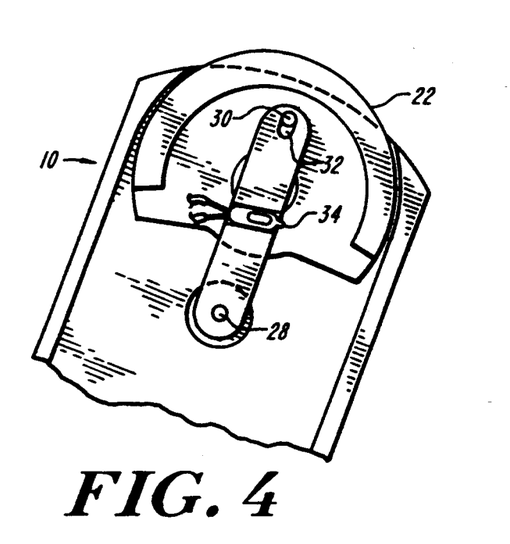
FIG. 4 is a side view of a portion of the arthrometer of FIG. 3 showing a detail of a switch positioning assembly.

This arrangement allows the orientation of the switch 34 to be adjusted relative to a principal axis 12a. Rotating the dial 22 displaces shaft 30 which in turn translates and rotates the arm 24 (since shaft 30 is fitted within the elongated aperture 32). Since the switch 34 is rigidly affixed to the arm 24, the orientation of switch 34 is controlled by rotation of the dial 22 in a vernier manner, permitting relatively fine adjustment. FIG. 4 shows the arthrometer 10 with the switch 34 oriented differently than in FIG. 3. This different orientation was achieved by rotating dial 22 to a different position than that shown in FIG. 3.

In alternate forms of the invention, the switch 34 directly shifts the angle shifted of switch by return of dial 22.

The aperture 32 of the illustrated embodiment is elongated to allow for a changing distance between the shaft 30 and the shaft 28 as the dial 22 is rotated. In FIG. 4 the shaft 30 is nearly maximally distant from the shaft 28, and therefore the shaft 30 is at one end of the aperture 32. In FIG. 3 the shaft 30 is closer to the shaft 28 and is at the other end of the aperture 32.

The bottom switch positioning assembly 20 contains identical and corresponding parts as the top assembly 18.

Referring again to FIG. 3, it can be seen that the mercury switches are arranged to monitor the angle A between the principal axis 12a and a vertical axis 42. The direction of the vertical axis 42 is defined by the direction of the force of gravity. The mercury switches are orientation sensitive, gravity-actuated switches. A switch 44 has a containment bottle 48, two conductive leads 46 which project into the bottle, and a bead of mercury 50. The switch 44, as shown in FIG. 3, is in a non-conductive state (i.e., there is an open circuit between the leads 46) because the switch is oriented so that the force of gravity has pulled the bead of mercury 50 away from the two leads 46. If the angle A was increased slightly (corresponding to the user squatting slightly lower during a knee-bend, as will be described more fully below), the bead of mercury 50 would slide to the other side of the bottle 48 and contact the ends of the leads 46, thus forming a short circuit between the leads 46. The switch 44 would then be in a conductive state. So the mercury switches can be preset to various orientations (by rotation of the dials) and for any given orientation a switch will change states whenever the angle between the principal axis 36 and the vertical axis 42 transitions through a particular corresponding value.

Figure 5:
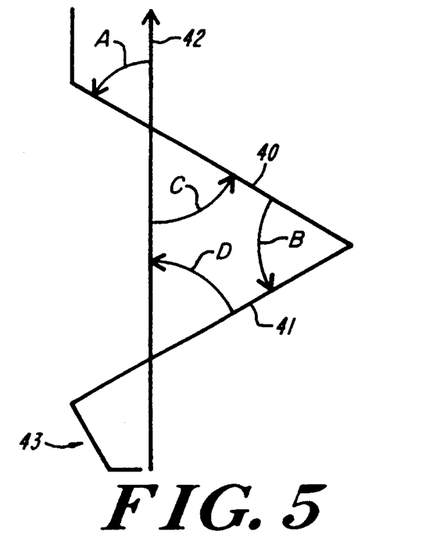
FIG. 5 is a stick figure of a human leg during the performance of a knee-bend.

FIG. 5 shows a stick figure of a user performing a knee bend. The mercury switches are arranged to monitor an angle A between a thigh 40 and the vertical axis 42. The knee flexure angle B can be approximated from the angle A. The angle A equals the angle C, and based on knowledge of the characteristics of samples of the human population (citation), the thigh and lower leg are approximately equal in length the angles C and D are the base angles of an isoceles triangle formed between the hip, knee, and ankle of the user, and, thus, angle C equals angle D. Since the three angles of any triangle sum to 180 degrees, the knee flexure angle B can be calculated once angles C and D are known. Since A equals C and C is approximately equal to D, the knee flexure angle B can be approximated according to the formula B = 180−2A. Angle A can be determined by adjusting the dial after a prior calibration of the dial against known angles.

It is reasonable to assume that the angle C equals the angle D because it is nearly universal that humans have a thigh ratio (i.e., the ratio of thigh to total leg length) of approximately 0.5, meaning that the length of the thigh 40 approximately is equal to the length of the lower leg 41. Because these lengths are approximately equal, and because of the added constraint that a standing knee bend must be performed with the user's center of gravity over the foot 43, the angle C nearly always equals the angle D during the performance of a standing knee-bend. Small devices of the thigh ratio have little effect on the measurements. Moreover, placement of the device 10 anywhere along the axis of the thigh 40 does not affect the accuracy.

During rehabilitation therapy the user often is instructed to perform repetitive knee-bends. Repetitive knee-bends are properly performed by beginning in a straight standing position (knee flexure angle B near 180 degrees) and then bending the knees and squatting down (decreasing the knee flexure angle) until a lower extreme point is crossed (e.g., knee flexure angle B equal to 90 degrees). Once the lower extreme point is serving as a reset angle, the user reverses direction and begins to "straighten up" (increasing the knee flexure angle B) until an upper extreme point is crossed serving as a reset angle (e.g., knee flexure angle B equal to 170 degrees). Once the upper extreme point is crossed the user again reverses direction and begins to squat down. The user oscillates between squatting down and straightening up, reversing direction every time one of the extreme points is crossed.

The arthrometer 10, as shown in FIG. 3, assists the user in performing proper knee-bends by indicating when the user crosses the extreme points, i.e., alternating between reset angles. Before beginning exercising, the user adjusts the dial 54 so that the switch 44 will change states at the desired, or prescribed, upper extreme point, and adjusts the dial 22 so that the switch 34 will change states at the desired, or prescribed, lower extreme point. The leads of both switches are connected to a network 100 that senses and indicates the state of the switches, while debouncing the switch signal.

In the preferred embodiment, when the network 100 senses a change in sates of switch 44 (indicating that the upper extreme point has been crossed) the network produces an audible tone indicating that the user should now reverse direction and begin squatting lower. Similarly, when the network 100 senses a change in the state of the switch 34 (indicating that the lower extreme point has been crossed) the network produces a second audible tone indicating that the user should again reverse direction and begin straightening out the knee and standing up. In some embodiments, if the network 100 senses that either extreme point is crossed and the user has failed to reverse direction, a continuous alarm tone is sounded indicating that the user should now reverse direction.

Figure 6:
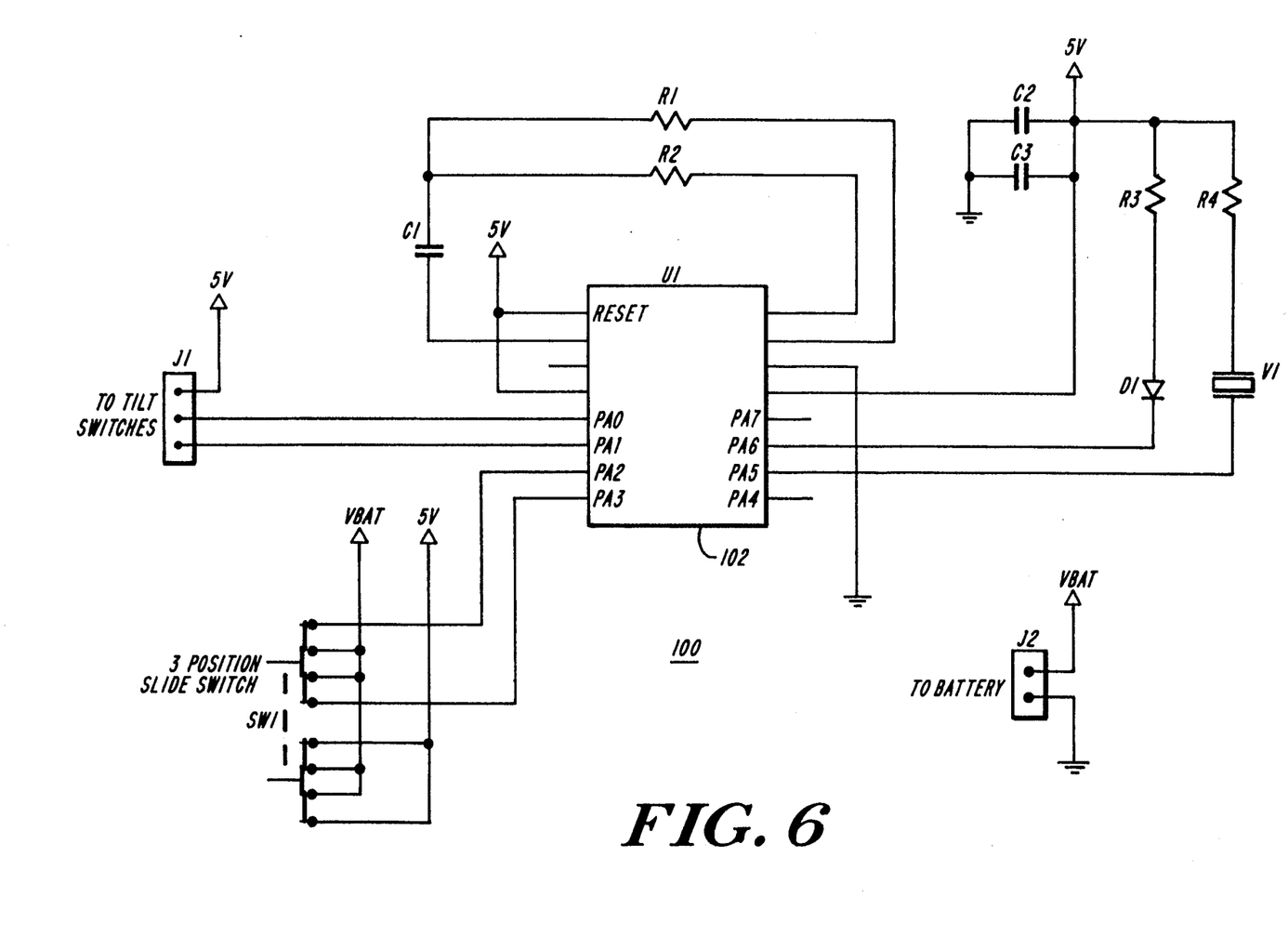
FIG. 6 is a schematic diagram of the monitoring and reporting network of the arthrometer of FIG. 1.

A preferred embodiment of the network 100 is shown in FIG. 6. The network 100 includes a microprocessor 102 having input ports programmed to detect the state of switches 34 and 44. The microprocessor 102 has an output port coupled to an audible tone generating device 106 (shown in FIG. 1). In the preferred embodiment, the microprocessor 102 is programmed to count the number of repetitions of knee-bends that have been performed. An exemplary program for microprocessor 102 is set forth in Table I.

In some embodiments, the network 100 produces visual signals (in addition to or instead of audible signals) indicative of when the user has crossed the extreme points. As shown in FIG. 1, the audible signals are emitted from the alarm sounder 106, and the visual signals are displayed on a display 108, such as an LCD display.

The top adjustment dial 22 and the bottom adjustment dial 54 are calibrated in terms of the knee flexure angle B, and the calibrations are displayed on outer surfaces 56, 58 of the dials so that the user can easily position the switches in the proper location for a prescribed knee bend.

To properly couple the illustrated embodiment of the invention to the thigh, the arthrometer 10 should be fixed to a side of the thigh so that a plane defined by axis 60 and axis 12a is substantially parallel to the vertical axis 42 throughout the knee-bend. Due to the elongate shape of the mercury switches, the illustrated embodiment will not function properly if the arthrometer 10 is strapped to the front or back of the thigh. This limitation can be overcome by use a two-axis, gravity-actuated switch, such as a spherically shaped switch, as is known in the art.

Figure 7:
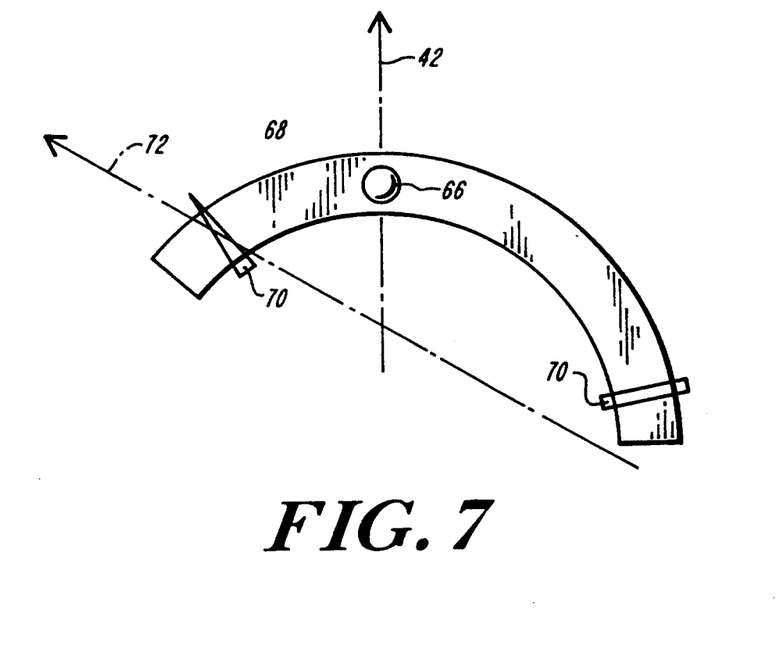
FIG. 7 is a side view of another embodiment of a gravity actuated sensor for use with an arthrometer according to the invention.

As will be apparent to those skilled in the art, although the illustrated embodiment is preferred due to its low manufacture cost and ease of use, many other embodiments of the arthrometer according to the invention are possible. For example, the switch positioning assembly could be of the lever type rather than of the dial type. Or the "gravity actuated" device could be of the arctuate type as shown in FIG. 7 having a ball 66 rolling along an arcuate track 68 and adjustable, optically sensitive, limit sensors 70 that sense the passage of the ball 66, and therefore monitor the angle between an axis 72 and the vertical axis 42. An analagous bubble within an arcuate fluid tube could be similarly configured. Alternatively, the "gravity actuated" device could be configured as a transducer coupled to a "see-saw" device that provides a continuous electronic output indicative of the angle between the sensor and the vertical axis. The limit sensing on such a device could be accomplished by a microprocessor monitoring of the electronic output signal.

TABLE I

```
/* Program ARTHRD.05C
/*
   Define the target hardware configuration
   to the compiler with *pragma statements.
*/
#include <HC705K1.05h>   /* K1 port and memory specifics */
#pragma vector ___RESET   @ 0x03fe ; /* Dummy vector so C6805 will be happy    */
#pragma vector SLEEP      @ 0x03fc ; /* SWI vector                             */
#pragma vector TIMER      @ 0x03fB ; /* Timer vector                           */
#pragma vector IRQ        @ 0x03fa ; /* IRQ vector                             */
#pragma mor @ 0x17 = 0x60; /* 3-pin R-C osc */
/* flag bit definitions */
#define cycle flag.7 /* flex/extend toggle */
/* portA bit positions */
#define Beeper   porta.6   /* beeper - output */
#define Led1     porta.5   /* led 1 - output */
#define Led2     porta.4   /* led 2 - output */
#define Mode2    porta.3   /* mode 2 - input */
#define Mode1    porta.2   /* mode 1 - input */
#define FLEX     porta.1   /* flex sensor - input */
```

TABLE I-continued

```
#define EXTD   porta.0   /* extend sensor - input */
#define hifreq 54
#define lofreq 108
#define rtif tscr.6          /* (tof .7) (rtif .6) */
#define CLRrtif tscr.2=1     /* (tof .3) (rtif .2) */
#define ledON Led1=0
#define ledOFF Led1=1
#define beepOFF Beeper=1
/* VARIABLES */
registerx inX;
registera inAC;
unsigned int i, count, freq, beepON, bpstate, bptime;
bits flag;
unsigned int sensval; /* debounce state */
/*** FUNCTIONS ***/
/**********************************************************
 * MAIN - Beginning of main program loop                   *
 **********************************************************/
void main(void)
{
    /* initialize variables and registers */
    porta = 0b01110000;
    ddra  = 0b01110000;
    pdra  = 0b01110000;
    count = 0;
    flag  = 0;
    freq  = iofreq;
    tscr  = 0;
    beepON = 0;
    bpstate = 0;
    sensval = 0;
for (;;)   /* infinite for loop */
  {
    if(lrtif)
      { if (tcntr >= count)
        { bpstate ^= 1;
          count += freq;
          if(beepON > 0)
          Beeper =0 /*bpstate*/;
        }
      }
    else   /* this part done once every debounce cycle */
    { CLRrtif;
      if(Model) bptime = 255; /* short beep */
      in(Mode2) bptime = 2; /* really long beep */
      switch (sensval)
      {
         case 0: if (FLEX || EXTD)
                  sensval++; /* If keypress then debounce */
                 break;
         case 1: if (FLEX || EXTD) /* If still keypress, execute */
                 { if((FLEX)&&(cycle))
                     { cycle = 0;
                       beepON = bptime;
                     }
                   if((EXTD)&&(!cycle))
                     { cycle = 1;
                       beepON = bptime;
                     }
                   if (Model) beepON = bptime;
                   sensval = 0xfe;
                 }
                 else
                   sensval = 0; /* no keypress */
                 break;
         case 0xfe: if ((FLEX==0) && (EXTD==0)) /* if keyup */
                    { if (Model)
                        beepON = 0;
                      sensval = 0xff; /* key up*/
                    }
                    break;
         case 0xff: sensval = 0;
      } /* end switch */
      if(beepON > 0)
        { beepON--;
          ledON;
        }
      else
        { ledOFF;
          beepOFF;
        }
    } /* end else (debounce cycle) */
```

TABLE I-continued

```
} /* end for */
} /* end main */
```

In some clinical settings, it is useful to measure only one limit excursion (e.g., only the lower or upper extreme point), so another useful embodiment may have only one switch positioning assembly and one gravity actuated sensor.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

Having described the invention, what is claimed as new and secured by Letters Patent is:

1. An arthrometer for monitoring an angle of flexure of an elongated body limb with respect to the portion of the body to which the limb is attached, comprising:
   A. an elongated housing extending along a principal axis,
   B. means for detachably coupling said housing to the limb whereby said principal axis is at a fixed orientation with respect to a central axis of the limb,
   C. first limit sensor affixed to said housing including:
      i. a first gravity-actuated switch coupled to said housing and responsive to orientation relative to a vertical axis, so that said first switch is in a first state when said first switch is oriented within a first range of orientations, and said first switch is in a second state when said first switch is oriented within a second range of orientations,
      ii. first switch positioning assembly including first venier means for adjustably orienting said first switch with respect to said principal axis whereby said first switch is in its first state when said principal axis is oriented within a first predetermined range of orientations measured with respect to the vertical axis and in its second state otherwise, and
   D. second limit sensor affixed to said housing including:
      i. a second gravity-actuated switch coupled to said housing and responsive to orientation relative to the vertical axis, so that said second switch is in a first state when said second switch is oriented within a third range of orientations, and said second switch is in a second state when said second switch is oriented within a fourth range of orientations, and
      ii. second switch positioning assembly including second vernier means for adjustably orienting said second switch with respect to said principal axis whereby said second switch is in its first state when said principal axis is oriented within a second predetermined range of orientations measured with respect to the vertical axis and in its second state otherwise,
wherein said first and second switches are mercury switches, and
wherein said first switch positioning assembly includes:
   i. first adjustment member and means for rotatably coupling said first adjustment member to said housing about an axis substantially perpendicular to said principal axis,
   ii. a first elongated adjustment arm extending between two ends thereof along a first arm axis, and means for rotatably coupling one of said ends to said housing about an axis substantially perpendicular to said principal axis, and means for slidably and rotatably coupling the other of said ends to said first adjustment member along a slide axis substantially parallel to said first arm axis and about an axis substantially perpendicular to said principal axis,
   iii. means for rigidly affixing said first switch to said first arm in a first predetermined orientation with respect to arm first arm axis, and
wherein said second switch positioning assembly includes:
   i. second adjustment member and means for rotatably coupling said second adjustment member to said housing about an axis substantially perpendicular to said principal axis,
   ii. a second elongated adjustment ann extending between two ends thereof along a second arm axis, and means for rotatably coupling one of said ends to said housing about an axis substantially perpendicular to said principal axis, and means for slidably and rotatably coupling the other of said ends to said second adjustment member along a slide axis substantially parallel to said second arm axis and about an axis substantially perpendicular to said principal axis, and
   iii. means for rigidly affixing said second switch to said second arm in a second predetermined orientation with respect to said second arm axis.

* * * * *